US00PP25811P2

(12) United States Plant Patent
Zaiger et al.

(10) Patent No.: US PP25,811 P2
(45) Date of Patent: Aug. 18, 2015

(54) INTERSPECIFIC TREE NAMED 'CRIMSON CARSON'

(50) Latin Name: ***Prunus* species**
Varietal Denomination: Crimson Carson

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 62 days.

(21) Appl. No.: 13/999,285

(22) Filed: Feb. 7, 2014

(51) Int. Cl.
*A01H 5/08* (2006.01)

(52) U.S. Cl.
USPC ..... Plt./180

(58) Field of Classification Search
USPC ..... Plt./180, 184, 186
CPC . A01H 5/0837; A01H 5/0862; A01H 5/0843; A01H 5/08
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Heavy and regular production of medium size fruit.
3. Fruit with attractive red skin color.
4. Fruit with very good flavor and eating quality.

1 Drawing Sheet

Botanical designation: Interspecific *Prunus* species.
Variety denomination: 'CRIMSON CARSON'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecifics, which are known to us, and mentioned herein, 'Flavorite' Interspecific (U.S. Plant Pat. No. 11,609), 'Flavor Queen' Interspecific (U.S. Plant Pat. No. 10,915), 'Flavor Royale' Interspecific (U.S. Plant Pat. No. 16,413) and our proprietary non-patented interspecific selections '17MA204', '75Z424', '368LD243', 42GA580 and 7HC244.

STATEMENT REGARDING FEDERALLY SPONSORED RESEARCH AND DEVELOPMENT

Not applicable.

ORIGIN OF THE VARIETY

The new and distinct variety of interspecific tree consists of the combination of (*Prunus salicina* and *Prunus armeniaca*) was originated by us in our experimental orchard located near Modesto, Calif. from seed of our open pollinated proprietary non-patented interspecific seedling with the field identification number '17MA204'. The interspecific non-patented seed parent (17MA204) originated as a first generation cross of our proprietary non-patented interspecific selections '75Z424' and '368LD243'. The interspecific seedling selection '75Z424' originated as a first generation seedling from the cross of 'Flavorite' Interspecific (U.S. Plant Pat. No. 11,609) with the proprietary non-patented Plumcot '42GA580'. '368LD243' originated from the cross of our interspecific non-patented proprietary seedling '7HC244' with 'Flavor Queen' Interspecific (U.S. Plant Pat. No. 7,420). A large number of these open pollinated seedlings were budded onto older established trees of 'Nemaguard' Rootstock (non-patented) to induce earlier maturity and fruit evaluation. Under close and careful observation the present seedling exhibited desirable tree and fruit characteristics and was selected in 2004 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific trees which consists of Plum and Plumcots is of large size, vigorous, upright growth and is a regular and productive bearer of medium size, red flesh fruit with very good flavor and eating quality. The fruit is further characterized by having attractive red skin, firm flesh that has good shipping and storage quality. In comparison to its immediate parent (17MA204) the fruit of the new interspecific variety is approximately 7 days earlier in maturity and a chilling requirement of approximately 600 hours at or below 45° F. compared to 700 hours. In comparison to the commercial variety 'Flavor Royale' Interspecific (U.S. Plant Pat. No. 16,413) the fruit of the new variety is approximately 7 days earlier in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 7 consecutive years. No alternate bearing observed.

*Fertility*.—Self-sterile, pollinator required.

*Density*.—Medium dense, usually pruned to vase shape to allow more sunlight to center of tree to enhance fruit color and health of fruit wood.

*Hardiness*.—Hardy in all stone fruit growing areas of California. Tree grown in USDA Hardiness Zone 9. Winter chilling requirement approximately 600 hours at or below 45° F.

Trunk:

*Size*.—Large. Average circumference of 57.2 cm at 20.3 cm above ground on a 8 year old tree.

*Stocky*.—Medium stocky.

*Texture*.—Medium shaggy, roughness increases with age.

*Color*.—Varies from 10YR 2/2 to 2.5Y 4/2.

Branches:

*Size*.—Medium. Average circumference 15.5 cm at 1.2 meters above ground.

*Surface texture*.—New growth relatively smooth. Mature growth medium rough, roughness increases with age.

*Lenticels*.—Average number 27 in 25.8 sq cm area. Average length 5.5 mm. Average width 2.0 mm. Color varies from 7.5YR 4/8 to 10YR 5/8.

*Color*.—New growth varies from 5GY 5/6 to 5R 3/4. Mature growth varies from 10YR 3/2 to 10YR 2/2, varies with age of growth.

Leaves:

*Size*.—Medium to large. Average length 103.9 mm. Average width 47.6 mm.

*Form*.—Oblanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins, glabrous. Lower surface relatively smooth except for ridges created by midrib and pinnate venation, glabrous.

*Petiole*.—Average length 11.8 mm. Average width 1.5 mm. Longitudinally grooved. Color varies from 7.5GY 5/6 to 5GY 4/8. Surface — glabrous.

*Glands*.—Type — globose. Size — small. Average length 0.7 mm. Average diameter 0.5 mm. Average number 3, varies from 2 to 4. Located primarily on base of the leaf blade and the upper portion of the petiole. Color varies from 5GY 6/8 to 2.5GY 6/8.

*Stipules*.—Average number 2. Average length 5.5 mm. Edges — pectinate. Color 5GY 6/8.

*Color*.—Upper surface varies from 5GY 3/6 to 7.5GY 3/4. Lower surface varies from 5GY 4/4 to 7.5GY 4/4. Midvein color varies from 5GY 6/6 to 5GY 5/8.

Flower buds:

*Size*.—Medium to large. Average length 9.2 mm. Average diameter 6.2 mm.

*Hardiness*.—Hardy with respect to California winters.

*Form*.—Conical, becomes more elongate as bud matures.

*Pedicel*.—Average length 7.9 mm. Average width 0.6 mm. Color varies from 2.5GY 6/8 to 5GY 7/6.

*Color*.—N 9.5/ (white).

*Number of buds per spur*.—Varies from 5 to 10, average number 7. Varies with age of spur.

Flowers:

*Blooming period*.—Date of First Bloom Feb. 20, 2013. Date of Petal Fall Mar. 2, 2013, varies slightly with climatic conditions.

*Size*.—Medium to large. Average height 10.8 mm. Average diameter 18.8 mm.

*Petals*.—Number — normally 5, alternately arranged to sepals. Size — medium. Average length 9.6 mm. Average width 8.4 mm. Form — obovate. Arrangement — overlapping. Margin — sinuate. Color N 9.5/ (white). Both upper and lower surfaces glabrous.

*Sepals*.—Number — normally 5, alternately arranged to petals. Size — small to medium. Average length 3.2 mm. Average width 2.6 mm. Shape — triangular. Margin — entire. Color — upper surface varies from 2.5GY 6/8 to 5GY 6/8. Lower surface varies from 2.5GY 6/6 to 5GY 5/8. Both upper and lower surfaces glabrous.

*Stamens*.—Average number per flower 33. Average filament length 7.2 mm. Filament color N 9.5/ (white). Anther color varies from 5Y 8/8 to 5Y 8/10.

*Pollen*.—Self sterile. Color varies from 5Y 7/8 to 5Y 7/10.

*Pistil*.—Number — normally one. Surface — glabrous. Average length 10.6 mm. Position of stigma an average of 1.1 mm above anthers. Color varies from 10Y 7/6 to 2.5GY 8/6.

*Fragrance*.—Heavy.

*Color*.—N 9.5/ (white).

*Number flowers per flower bud*.—Varies from 1 to 4, average number 3.

*Pedicel*.—Average length 8.7 mm. Average width 0.6 mm. Color varies from 2.5GY 7/8 to 2.5GY 6/6.

Fruit:

*Maturity when described*.—Firm ripe.

*Date of first picking*.—May 28, 2013.

*Date of last picking*.—Jun. 7, 2013, varies slightly with climatic conditions.

*Size*.—Medium. Average diameter 50.8 mm. Average transversely in suture plane 59.0 mm. Average weight 105.1 grams, varies slightly with fertility of the soil, amount of thinning and climatic conditions.

*Form*.—Globose.

*Suture*.—Nearly smooth to very slightly lipped, extends from base to apex.

*Ventral surface*.—Nearly smooth.

*Apex*.—Rounded.

*Base*.—Flat.

*Stem cavity*.—Rounded to slightly elongated in the suture plane. Average depth 5.7 mm. Average diameter 5.2 mm.

Stem:

*Size*.—Medium. Average length 14.3 mm. Average diameter 1.5 mm.

*Color*.—Varies from 5GY 6/6 to 5GY 5/6.

Flesh:

*Ripens*.—Normally even, some fruit slightly earlier at apex.

*Texture*.—Firm.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, good balance between acid and sugar.

*Juice*.—Heavy amount, enhances flavor.

*Brix*.—Average Brix 13.4°, varies slightly with amount of fruit per tree and climatic conditions.

*Color*.—Varies from 5R 3/10 to 5Y 9/2.

*Pit cavity*.—Average length 23.0 mm. Average width 20.0 mm. Average depth 5.0 mm. Color 5R 3/10.

Skin:

*Thickness*.—Medium.

*Surface*.—Smooth.

*Bloom*.—Moderate amount.

*Tendency to crack*.—None.

*Color*.—Ground color varies from 2.5Y 8.5/6 to 5Y 9/4. Overspread with 5R 3/8 to 5R 2/4.

*Tenacity*.—Tenacious to flesh.

*Astringency*.—Slight to none.

Stone:

*Type*.—Clingstone.

*Size*.—Medium. Average length 22.6 mm. Average width 19.1 mm. Average thickness 8.7 mm.

*Form*.—Ovoid.

*Base*.—Flat.

*Apex*.—Acuminate, average length 1.2 mm.

*Surface*.—Slightly pitted throughout.

*Sides*.—Unequal, one side extending further from suture plane.

*Ridges*.—A small ridge on each side of suture extending from base to apex.

*Tendency to split*.—None.

*Color*.—Varies from 5YR 4/8 to 7.5YR 5/8 when dry.

Kernel:

*Size*.—Small to medium. Average length 12.9 mm. Average width 9.3 mm. Average depth 4.3 mm.

*Form*.—Ovoid.

*Viability*.—Partially viable, some embryos with incomplete development.

*Skin color*.—Varies from 5Y 9/4 to 7.5Y 9/4.

Use: Dessert.

*Market*.—Local and long distance.

Keeping quality: Good, held firm in cold storage for 3 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

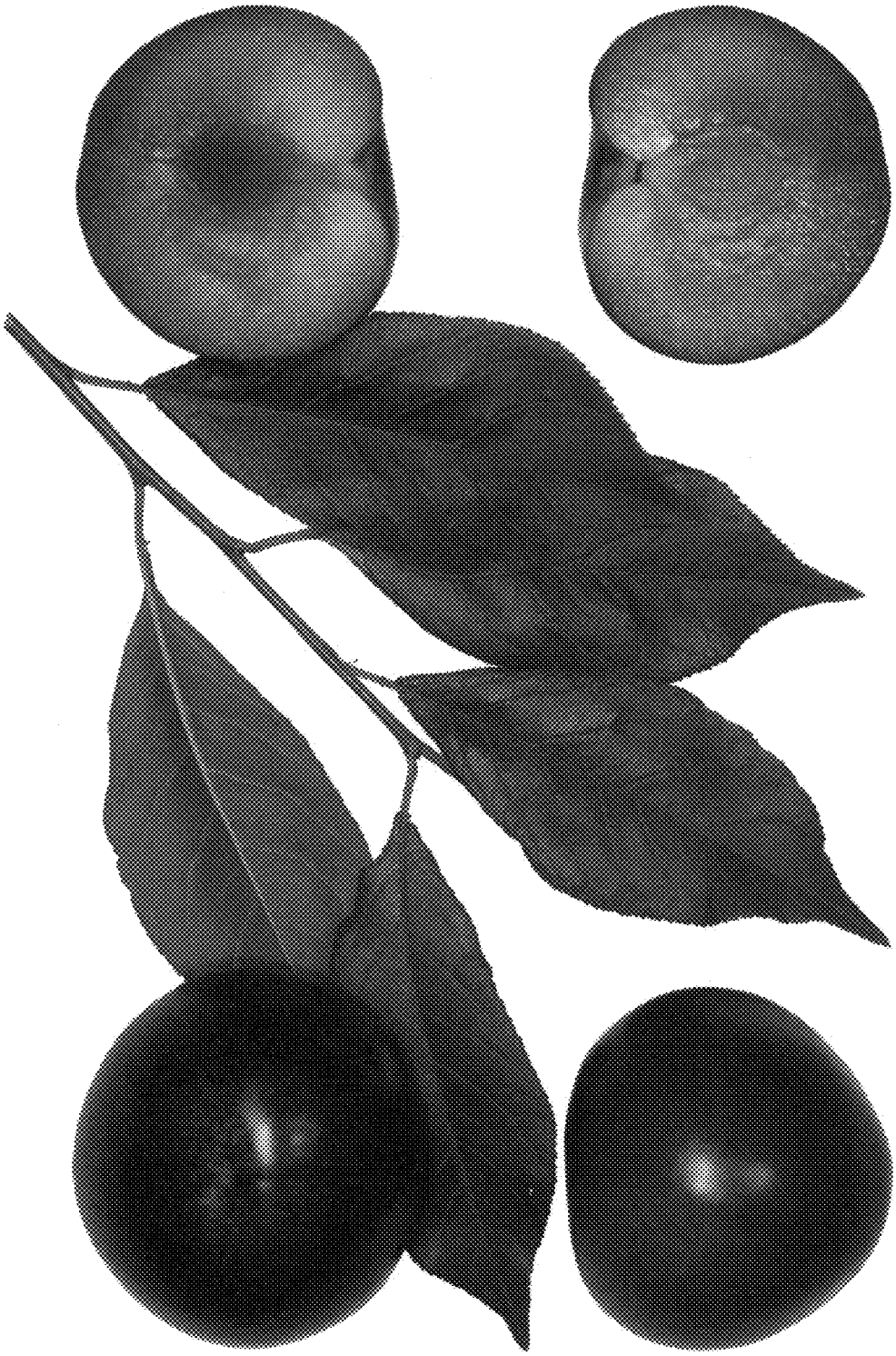

* * * * *